United States Patent [19]

Sisson et al.

[11] 4,322,976

[45] Apr. 6, 1982

[54] MECHANICAL VIBRATION ANALYZER

[75] Inventors: Edwin D. Sisson, Worthington; Donn V. Stoutenburg, Westerville; Glen H. Thomas, Worthington, all of Ohio

[73] Assignee: IRD Mechanalysis, Inc., Columbus, Ohio

[21] Appl. No.: 137,551

[22] Filed: Apr. 4, 1980

[51] Int. Cl.³ .............................................. G01N 29/04
[52] U.S. Cl. .................................... 73/659; 324/77 A
[58] Field of Search ......................... 73/659, 660, 579; 324/77 A, 77 B, 77 E, 77 G; 340/715, 753, 754, 766

[56] References Cited

U.S. PATENT DOCUMENTS 3,029,385  4/1962  Steinbrenner et al. ............... 73/659

OTHER PUBLICATIONS

Henry, "An LED-Readout Audio Power Meter", *Popular Electronics*, Mar. 1976, pp. 35-38.

*Primary Examiner*—Anthony V. Ciarlante
*Attorney, Agent, or Firm*—Mueller and Smith

[57] ABSTRACT

A visual graphical display of instantaneous mechanical vibration versus frequency over a selected frequency spectrum is presented to provide a vibration analyst with a prompt overall visual impression of the mechanical vibration characteristics of a rotating device which is under surveillance. In an alternative application, the visual display permits a rapid adjustment of an electrical bandpass filter of an associated vibration analyzer. The device employs several trains of diodes which are arranged so that one or more diode in each train is illuminated at any one moment.

6 Claims, 4 Drawing Figures

MECHANICAL VIBRATION ANALYZER

BACKGROUND OF THE INVENTION

1. Field of the Invention

The present invention relates to an improvement in mechanical vibration analyzers and more particularly to a mechanical vibration analyzer which includes a "quiklook" visible display octave analyzer.

2. Description of the Prior Art

Mechanical vibration analyzers are well-known. See U.S. Pat. Nos. 2,711,647, 3,205,713 and 3,938,394. Octave band analyzers and fractional octave band analyzers are well-known in the electronics industry as devices for instantaneously observing the relative wave energy content of a multi-frequency wave phenomenon, e.g., an acoustical signal.

In the past, mechanical vibration analyzer equipment has included a mechanical vibration detector which converts instantaneous mechanical vibrations into corresponding cyclic electrical signals having wave components at multiple electrical frequencies. The vibration analyzers also include narrow band electrical filters for selecting various electrical frequency components within a narrow range of frequencies. The instantaneous amplitude of the electrical wave signals within the narrow filter band is observed. For example, the amplitude of the narrow band electrical signals is displayed in a voltmeter scale which may be suitably calibrated to indicate the corresponding mechanical vibration values, such as displacement, velocity, acceleration.

By employing variable frequency band filters in prior art mechanical vibration analyzers, it is possible for the operator to scan through multiple frequency ranges and observe the instantaneous mechanical vibration amplitude in each observed frequency range. This is time-consuming, particularly at lower frequencies where the electrical filter components require substantial time lapse to achieve equilibrium conditions. At any one instant, the prior art devices display only the amplitude existing for the particular frequency band selected by the operator. If the operator is seeking peak amplitude phenomena, it may be necessary for the operator to conduct a frequency scan over the entire spectrum of frequencies which the mechanical vibration analyzer is capable of observing.

Accordingly it would be desirable to have a mechanical vibration analyzer which can supply a qualitative indication to the operator of the instantaneous mechanical vibration amplitudes in various frequency bands over the range of vibration frequencies which the analyzer is capable of observing. The operator thereby can quickly and effectively target the range of vibration frequencies which should be subjected to more intensive observation in the analyzer equipment.

Recent developments in vibration analyzers having digital readout presentations have created a difficulty in fine tuning the analyzer filters. Prior art analyzers have meter-deflection readout presentations providing a useful fine tuning indicator for the analyzer filters. See U.S. Pat. No. 3,228,235. The operator could easily detect peak deflections and thereby fine tune the filter.

A buckets and arrows technique has been described in copending U.S. patent application Ser. No. 76,030, filed Sept. 17, 1979, which requires supplementary apparatus for the fine tuning function in vibration analyzers having digital readout presentations.

A quick visual fine tuning device for an analyzer filter would be desirable in a vibration analyzer having a digital readout display.

SUMMARY OF THE INVENTION

The present invention is an improvement in prior art mechanical vibration analyzer equipment of the type which includes (1) a vibration detector for converting mechanical vibrations into a corresponding cyclic electrical signal;
(2) an electrical filter for selecting narrow band portions of the electrical wave components of the cyclic electrical signal; and
(3) electrical circuit means for observing a selected narrow band portion of the cyclic electrical signal.

According to this improvement, the cyclic electrical signal is applied to the electrical input terminal of an octave band analyzer which has a visible display formed from a series of parallel diode trains and has multiple filter means, one each for each of the parallel diode trains whereby the cyclic electrical signal can be filtered into a series of selected frequency band components and the amplitude of each of the selective portions can be visibly displayed on the related one of the parallel diode trains. Accordingly the operator of the vibration analyzer can visibly observe the overall nature of the mechanical vibrations throughout the spectrum of frequencies covered by the octave band analyzer.

This improvement also functions as a fine tuning device for the filter of a vibration analyzer which has a digital readout presentation. The filter is connected in series with the octave band analyzer. The output signal from the filter will illuminate one or perhaps two of the parallel diode trains of the octave band analyzer. The operator can easily fine tune the filter by observing the peak response in the appropriate one of the diode trains.

DESCRIPTION OF THE PREFERRED EMBODIMENT(S)

Figure 1:
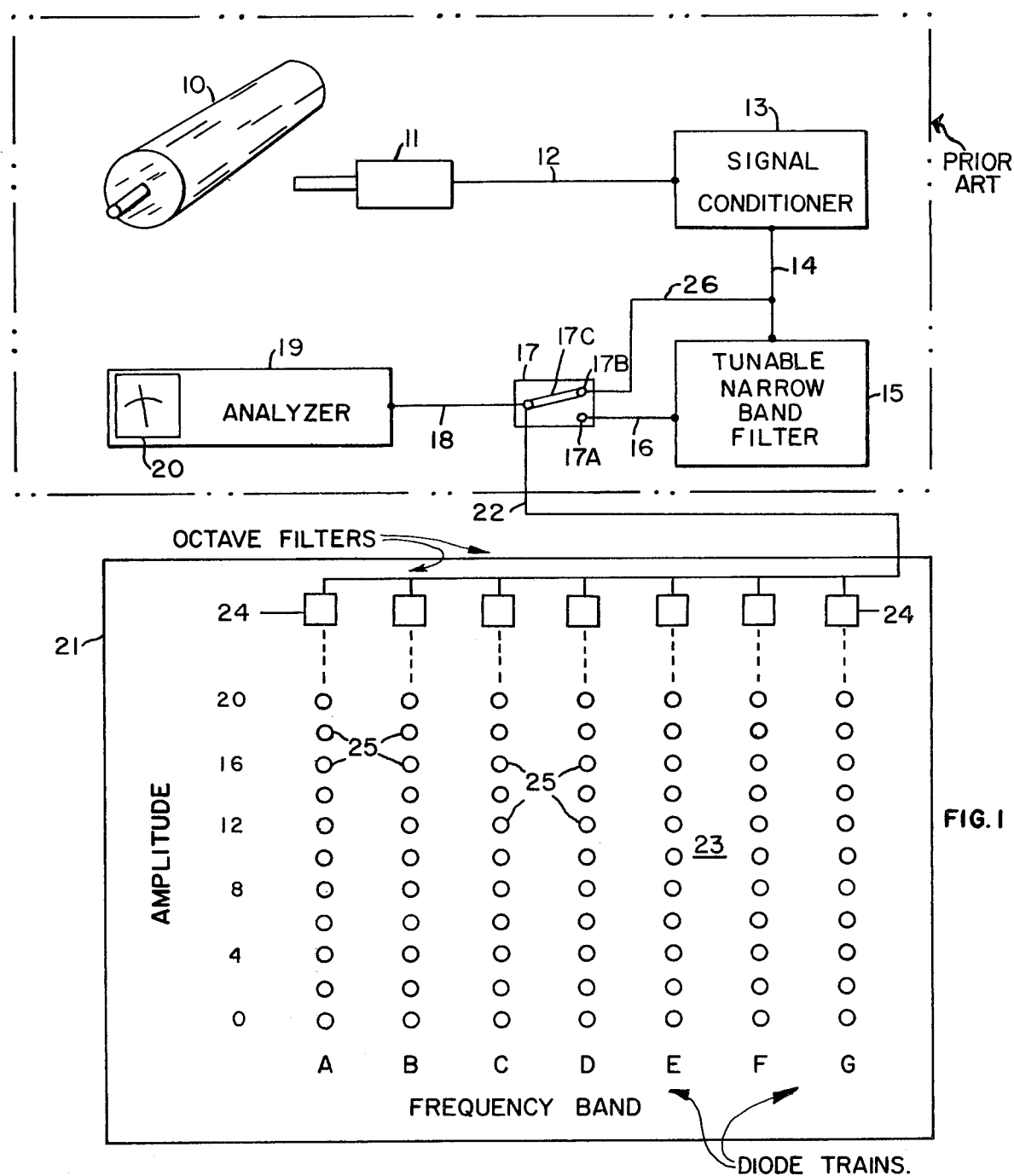
FIG. 1 is a schematic illustration showing a prior art mechanical vibration analyzer installation to which the present improvement has been incorporated.

As shown in FIG. 1, the prior art mechanical vibration analyzer installations are applied to sources of cyclic mechanical vibration such as a rotor 10. The cyclic mechanical vibrations of the rotor 10 are detected by a vibration detector 11 and delivered through a conductor 12 to a signal conditioner 13 which develops an output signal in the conductor 14 corresponding to the instantaneous mechanical vibrations of the rotor 10. The conductor 14 is connected to a narrow band filter 15 which selects those electrical frequency components of the cyclic electrical signal within a selected band of frequencies and delivers those electrical signal components through a conductor 16, a switch 17 and a conductor 18 to an analyzer 19 which frequently includes a voltmeter 20 suitably calibrated in units corresponding to the mechanical vibration of the rotor 10.

The vibration detector 11 can be responsive to the instantaneous displacement of the rotor 10 or to the instantaneous velocity of the rotor 10 or to the instantaneous acceleration of the rotor 10. Depending upon which phenomenon of the mechanical vibration is observed by the detector 11, the signal conditioner 13 will convert the electrical signal into a useful form for the filter 15 and analyzer 19, e.g., an acceleration-related signal can be integrated once to the corresponding velocity-related signal or integrated twice to the corresponding displacement signal.

According to the present invention an octave band analyzer 21 is connected through a conductor 22 to the base of switch 17. The switch 17 has a switch arm 17c which contacts either terminal 17b or 17a. When the switch arm 17c contacts terminal 17a, the filter 15 is connected in series with the analyzer 19 and also in series with the octave band analyzer 21. When the switch arm 17c contacts terminal 17b, the filter 15 is bypassed through conductor 26. The vibration signal is delivered directly from the signal conditioner 13 through conductor 14, conductor 26, switch 17, conductor 18 to the analyzer 19 and also through the conductor 22 to the octave band analyzer 21.

The octave band analyzer 21 includes a matrix 23 of individual diodes 25 which are aligned in trains labeled A, B, C, D, E, F, G and in rows labeled 0, 2, 4, 6, 8, 10, 12, 14, 16, 18, 20.

For each of the diode chains A, B, C, D, E, F, G there is an octave filter 24 which receives the cyclic electrical signal from the conductor 22 and delivers those selected frequency components of that signal to the train of diodes 22 through circuitry which illuminates one or more of the diodes 25 in each train.

Each of the octave band filters 24 is selected to pass a selected frequency of electrical wave components drawn from the cyclic electrical signal. Conveniently, the selected frequency bands differ by one octave or by an aliquot portion of an octave such as a half-octave or a third-octave. In a preferred embodiment having thirteen diode trains, the filters 24 and corresponding diode trains carry out the following filter functions.

| Diode Train | Frequency Range, Hertz |
|---|---|
| 1 | 2-4 |
| 2 | 4-8 |
| 3 | 8-16 |
| 4 | 16-31 |
| 5 | 31-62 |
| 6 | 62-125 |
| 7 | 125-250 |
| 8 | 250-500 |
| 9 | 500-1000 |
| 10 | 1000-2000 |
| 11 | 2000-4000 |
| 12 | 4000-8000 |
| 13 | 8000-16,000 |

The amplitude lines are calibrated in useful mechanical vibration units such as mils (thousandths of inches of mechanical displacement), inches per second; g's (gravitational constant); or voltage (decibels). The parameters of the circuitry are selected to yield the desired calibration units.

Operation

The operator assembles the mechanical vibration analysis apparatus and particularly the vibration detector 11 and signal conditioner 13 in suitable physical relationship to the rotor 10 under investigation. As the rotor is turning at a selected speed, usually its normal operating speed, the switch 17 has its switch arm 17c contacting terminal 17b, i.e., the filter 15 is bypassed.

Figure 2:
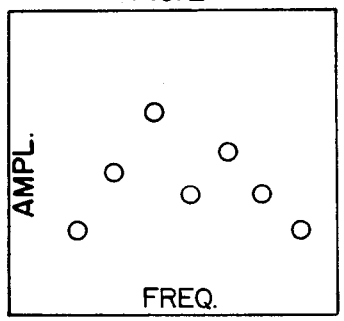
FIGS. 2, 3, 4 are plan views of typical visible displays resulting from the present equipment.
Figure 3:
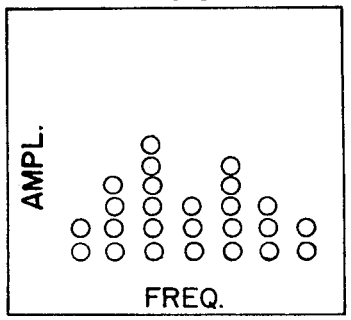
Figure 4:
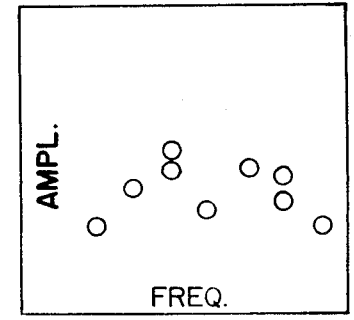

The octave band filter 21 will provide to the operator an instantaneous visible display of the relative magnitude of mechanical vibration in each of the selected frequency bands A, B, C, D, E, F, G. The display may take on several forms of presentation as shown in FIGS. 2, 3, 4 which are plan views of a typical visible display of illuminated diodes as seen through a translucent glass plate of the display device. In FIG. 2, only one diode in each of the trains A–G is illuminated at each instant. In FIG. 3 all of the diodes below a selected diode in each train are illuminated at each instant. In FIG. 4 one or occasionally two sequential diodes in each train are illuminated at each instant.

The operator by inspecting the visible display as seen in FIGS. 2, 3, 4 can determine which frequency band is experiencing maximum mechanical vibration and can quickly direct attention to that high amplitude frequency range.

Filter Fine Tuning

When the vibration analyzer 19 employs an observation device 20 which does not include a scale deflecting meter but instead employs a digital readout presentation, the present device provides simplified tuning of the filter 15. The filtering is achieved with the switch 17 having its switch arm 17c in contact with the terminal 17a. In this presentation the vibration signal from the signal conditioner 13 is delivered through conductor 14. A selected band of frequencies is passed through the filter 15 along conductor 16, switch 17, conductor 18 to the analyzer 19. The precision of the analyzer 19 is enhanced when the filter 15 has its passband centered at the frequency of peak vibration phenomena. The signal from the conductor 16 is delivered through the switch 17 and conductor 22 to the octave band analyzer 21. Depending upon the frequency at which the filter 15 is tuned, one or more of the filters 24 will pass electrical signals to one or more of the related diode trains A, B, C, D, E, F, G. The operator can selectively adjust the passband of the filter 15 by observing peak indications on the appropriate diode train and thereby achieve visually and manually a fine tuning of the filter 15 to optimize the results obtained in the vibration analyzer 19.

We claim:
1. A vibration analyzer comprising:
   vibration detector means for converting mechanical vibrations into a corresponding cyclic electrical signal;
   an electrical filter having an input for receiving said electrical signal and manually actuable for tuning within a wide range of electrical frequencies to select narrow band portions thereof for submittal at an output;
   electrical circuit means having an input and including a visual readout for observing amplitude and frequency values within a said narrow band portion of said range of electrical frequencies selected by said filter actuation;
   a visible display comprised of a plurality of light emitting diode trains mutually disposed in parallel adjacency to provide a spectral readout of amplitude and frequency substantially for said wide range of electrical frequencies;
   a plurality of octave filters each selecting a unique band of said frequencies within said wide range thereof;

each said train of light emitting diodes corresponding to and responsive to one of said octave filters and each said train including means for illuminating at least one unique diode in the train corresponding to the instantaneous amplitude of said selected unique frequency band; and switch means for coupling said plurality of octave filters to receive said electrical signal and alternately for coupling said circuit means input and said plurality of octave filters with said filter output.

2. The vibration analyzer of claim 1 wherein a single one of the said diodes in each of said diode trains is illuminated at any instant.

3. The vibration analyzer of claim 1 wherein a single one or a pair of adjacent ones of the diodes in each train is illuminated at any instant.

4. The vibration analyzer of claim 1 wherein each diode in each train is illuminated only when all of the diodes below it in the same train are illuminated.

5. The improvement of claim 1 wherein each of the said octave filters is adapted to select electrical frequencies substantially within a fractional portion of a frequency octave.

6. The vibration analyzer of claim 1 in which said switch means simultaneously couples said circuit means input to receive said electrical signal when coupling said plurality of active filters to receive said electrical signal.

* * * * *